United States Patent
Mullick et al.

(10) Patent No.: US 9,277,902 B2
(45) Date of Patent: Mar. 8, 2016

(54) METHOD AND SYSTEM FOR LESION DETECTION IN ULTRASOUND IMAGES

(71) Applicant: General Electric Company, Schenectady, NY (US)

(72) Inventors: Rakesh Mullick, Bangalore (IN); Vivek Prabhakar Vaidya, Bangalore (IN); Fei Zhao, Niskayuna, NY (US); Xiaoxing Li, Blacksburg, VA (US); Vidya Kamath, Niskayuna, NY (US); Kunlin Cao, Niskayuna, NY (US); Soma Biswas, Bangalore (IN)

(73) Assignee: General Electric Company, Niskayuna, NY (US)

( * ) Notice: Subject to any disclaimer, the term of this patent is extended or adjusted under 35 U.S.C. 154(b) by 154 days.

(21) Appl. No.: 14/088,068

(22) Filed: Nov. 22, 2013

(65) Prior Publication Data

US 2015/0148677 A1 May 28, 2015

(51) Int. Cl.
*A61B 8/08* (2006.01)
*A61B 8/14* (2006.01)
*A61B 8/00* (2006.01)
*G06T 7/00* (2006.01)
*G06T 7/40* (2006.01)

(52) U.S. Cl.
CPC ............... *A61B 8/5223* (2013.01); *A61B 8/085* (2013.01); *A61B 8/14* (2013.01); *A61B 8/4483* (2013.01); *G06T 7/0012* (2013.01); *G06T 7/0085* (2013.01); *G06T 7/403* (2013.01); *G06T 2207/10132* (2013.01); *G06T 2207/30068* (2013.01); *G06T 2207/30096* (2013.01)

(58) Field of Classification Search
CPC ................................. A61B 8/00; A61B 8/5223
See application file for complete search history.

(56) References Cited

U.S. PATENT DOCUMENTS

| | | | |
|---|---|---|---|
| 7,025,724 B2 | 4/2006 | Adam et al. | |
| 7,379,950 B2 | 5/2008 | Sato et al. | |
| 7,466,848 B2 | 12/2008 | Metexas et al. | |
| 7,515,743 B2 | 4/2009 | Kiraly et al. | |
| 2007/0242864 A1* | 10/2007 | Slabaugh et al. | 382/128 |
| 2009/0264758 A1* | 10/2009 | Fujita et al. | 600/443 |
| 2011/0182495 A1* | 7/2011 | Sun et al. | 382/141 |
| 2012/0243757 A1 | 9/2012 | Funka-Lea et al. | |
| 2014/0163369 A1* | 6/2014 | Nair | 600/437 |

OTHER PUBLICATIONS

Slabaugh, Greg; Unal, Gozde; Fang, Tong; and Wels, Michael; "Ultrasound-Specific Segmentation via Decorrelation and Statistical Region-Based Active Contours", Proceedings of the 2006 IEEE Computer Society Conference on Computer Vision and Patter Recognition (8 pgs.).

Wang, Zhe; Slabaugh, Greg; Unal, Gozde; Fang, Tong; "Registration of Ultrasound Images Using an Information-Theoretic Feature Detector", IEEE ISBI 2007; (4 pgs.).

(Continued)

*Primary Examiner* — Peter Luong
(74) *Attorney, Agent, or Firm* — Seema S. Katragadda

(57) ABSTRACT

A method is provided for detecting lesions in ultrasound images. The method includes acquiring an ultrasound image, generating a Fisher-tippett (FT) distribution-based edge feature map from the acquired ultrasound image, generating gradient concentration (GC) scores for pixels of the acquired ultrasound image using the FT distribution-based edge feature map, and identifying a candidate lesion region within the acquired ultrasound image based on the GC scores.

25 Claims, 13 Drawing Sheets

(56) References Cited

OTHER PUBLICATIONS

Coupe, Pierrick; Hellier, Pierre; Kervrann, Charles; and Barillot, Christian; "Nonlocal Means-Based Speckle Filtering for Ultrasound Images", IEEE Transactions on Image Processing, vol. 18, No. 10, Oct. 2009 (9 pgs.).

Wong, Alexander; and Jacob Scharcanski; "Fisher-Tippett Region-Merging Approach to Transrectal ultrasound Prostate Lesion Segmentation", IEE Transactions on Information Technology in Biomedicind, vol. 15, No. 6, Nov. 2011 (8 pgs.).

\* cited by examiner

| | SENSITIVITY =91% | SENSITIVITY =97% | SENSITIVITY =99% |
|---|---|---|---|
| CANDIDATE GENERATION | FP/IMAGE=6.73 | FP/IMAGE=9.65 | FP/IMAGE=12.2 |
| GLCM | FP/IMAGE=4.16 | FP/IMAGE=6.67 | FP/IMAGE=9.09 |
| INTENSITY MFs | FP/IMAGE=1.46 | FP/IMAGE=3.98 | FP/IMAGE=7.31 |
| INTENSITY + CURVATURE MFs | FP/IMAGE=1.19 | FP/IMAGE=2.22 | FP/IMAGE=3.03 |

FIG. 12

METHOD AND SYSTEM FOR LESION DETECTION IN ULTRASOUND IMAGES

BACKGROUND

Breast cancer is one of the leading causes of cancer related deaths in women across the world. Early detection of breast cancer plays an important role in reducing the cancer related deaths. Recently, the use of ultrasound imaging as a breast cancer screening tool has increased considerably, especially in developing countries. In addition to being relatively inexpensive and safe, using ultrasound images as an adjunct screening tool may provide improved detection sensitivity, especially for young women with relatively dense breast tissue.

But, known methods for detecting lesions in ultrasound images of the breast are not without disadvantages. For example, scanning the patient with the ultrasound probe is highly operator dependent, which may result in inconsistent and/or inaccurate ultrasound scans. Moreover, the relatively low quality of ultrasound images and the addition of artifacts such as speckle noise, shadows, ringing, and/or the like may increase the difficulty of lesion detection within ultrasound images. Known methods for detecting lesions in ultrasound images of the breast may also do a relatively poor job of accounting for the significant variations in the shape, size, echogenicity, and margin characteristics of breast lesions.

BRIEF DESCRIPTION

In an embodiment, a method is provided for detecting lesions in ultrasound images. The method includes acquiring an ultrasound image, generating a Fisher-tippett (FT) distribution-based edge feature map from the acquired ultrasound image, generating gradient concentration (GC) scores for pixels of the acquired ultrasound image using the FT distribution-based edge feature map, and identifying a candidate lesion region within the acquired ultrasound image based on the GC scores.

In an embodiment, an ultrasound system includes an ultrasound transducer for transmitting and receiving ultrasound signals to and from an area of interest, a receiver for receiving the ultrasound signals, and a processor coupled to the ultrasound probe. The processor is programmed to acquire an ultrasound image, generate a Fisher-tippett (FT) distribution-based edge feature map from the acquired ultrasound image, generate gradient concentration (GC) scores for pixels of the acquired ultrasound image using the FT distribution-based edge feature map, and identify a candidate lesion region within the acquired ultrasound image based on the GC scores.

In an embodiment, a method is provided for detecting lesions in ultrasound images. The method includes identifying a candidate lesion region within an ultrasound image, calculating multi-scale topological texture features for the candidate lesion region from the ultrasound image, and classifying the candidate lesion region as a lesion or normal tissue using a classifier.

BRIEF DESCRIPTION OF THE DRAWINGS

FIG. 12 is a table illustrating sensitivity versus false detections for the experimental evaluation shown in FIG. 11.

DETAILED DESCRIPTION

Figure 1:
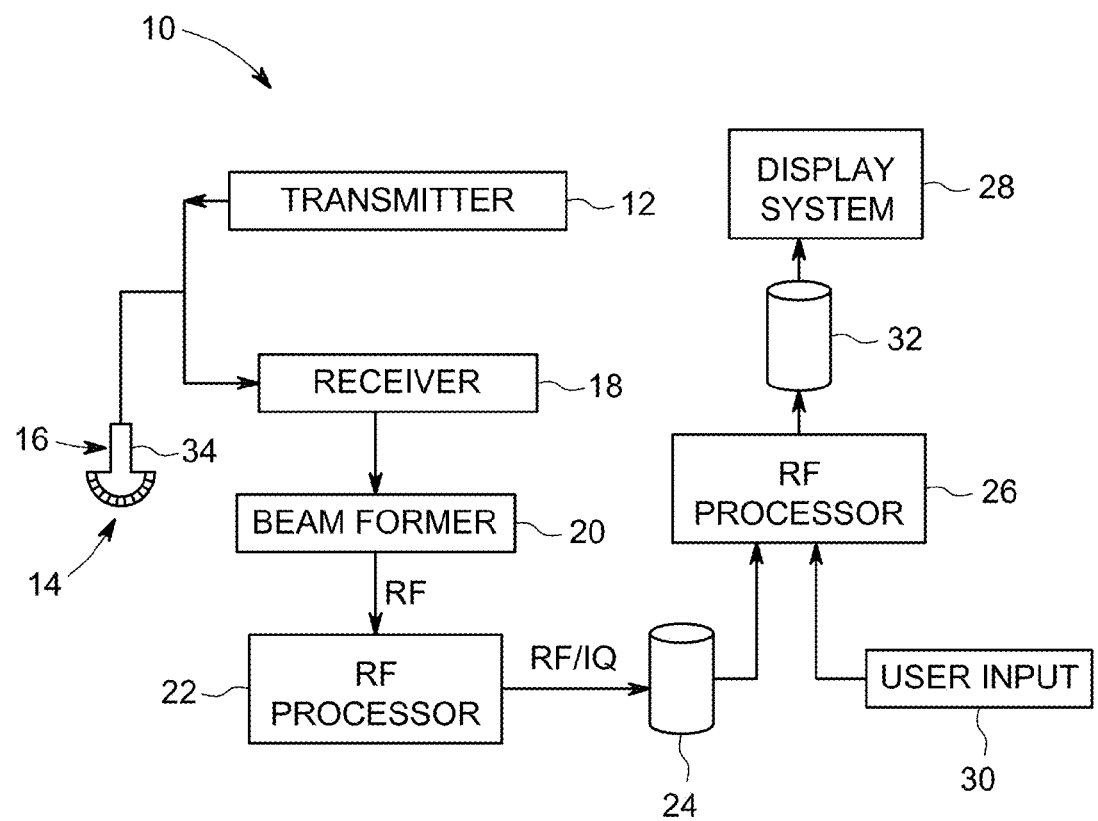
FIG. 1 is a block diagram of an ultrasound system in which various embodiments may be implemented.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and/or the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide ultrasound systems and methods for detecting lesions in ultrasound images, which may include acquiring an ultrasound image and generating a Fisher-tippett (FT) distribution-based edge feature map from the acquired ultrasound image, generating gradient concentration (GC) scores for pixels of the acquired ultrasound image using the FT distribution-based edge feature map, and identifying a candidate lesion region within the acquired ultrasound image based on the GC scores.

Various embodiments provide ultrasound systems and methods for detecting lesions in ultrasound images, which may include identifying a candidate lesion region within an ultrasound image, calculating multi-scale topological texture features for the candidate lesion region from the ultrasound image, and classifying the candidate lesion region as a lesion or normal tissue using a classifier.

The systems and methods described and/or illustrated herein may provide automatic lesion/cancer detection in ultrasound images. For example, the systems and methods described and/or illustrated herein may provide automatic detection of lesions in breast ultrasound images. A technical effect of at least some embodiments is automatic detection of lesions in ultrasound images. A technical effect of at least some embodiments is that the methods described and/or illustrated herein are relatively fast as compared to at least some known lesion detections methods. For example, the methods described and/or illustrated herein may be used as a relatively fast candidate lesion detection step in two-dimensional (2D) and/or three-dimensional (3D) ultrasound images.

A technical effect of at least some embodiments is the reduction of false detections. For example, the methods described and/or illustrated herein may relatively accurately localize potential masses (i.e., lesions) that require further evaluation with relatively low false detections. A technical effect of at least some embodiments is the reduction of false detections while maintaining a relatively high sensitivity. A technical effect of at least some embodiments is the ability to detect lesions of different sizes and/or shapes. A technical effect of at least some embodiments is a relatively fast and efficient approach for detecting lesions that is able to handle a relatively large amount of data (e.g., the relatively large in 3D images such as, but not limited to, 3D ultrasound images of the breast). For example, the methods described and/or illustrated herein may be used to reduce the overall computation time of detecting lesions while maintaining a relatively high detection rate. A technical effect of at least some embodiments is the ability to account for the relatively significant variations in the shape, size, echogenicity, and margin characteristics of lesions.

A technical effect of at least some embodiments is the ability to use the methods described and/or illustrated herein in conjunction with (e.g., feeding the candidate lesion regions identified by the methods described and/or illustrated herein into) more computationally expensive computer-aided detection (CAD) methods such as, but not limited to, a texture-based analysis, a machine learning method, and/or the like.

FIG. 1 is a block diagram of an ultrasound system 10 in which various embodiments may be implemented. The ultrasound system 10 may be used, for example, to acquire ultrasound data and generate ultrasound images. The ultrasound system 10 includes a transmitter 12 that drives an array of acoustic elements 14 within or formed as part of an ultrasound transducer 16 to emit pulsed ultrasonic signals into a body or other volume. The ultrasonic signals are back-scattered from density interfaces and/or structures in the body or other volume (e.g., blood cells, fatty tissue, and/or muscular tissue in a body) to produce echoes that return to the acoustic elements 14. The echoes are received by a receiver 18. The received echoes are passed through beamforming electronics 20, which performs beamforming and outputs an RF signal. The RF signal then passes through an RF processor 22. The RF processor 22 may include a complex demodulator (not shown) that demodulates the RF signal to form IQ data pairs representative of the echo signals. The RF or IQ signal data may then be routed directly to a memory 24 for storage (e.g., temporary storage).

The ultrasound system 10 also includes a signal processor 26 to process the acquired ultrasound information (e.g., RF signal data or IQ data pairs) and prepare frames of ultrasound information for display on a display system 28. The signal processor 26 is adapted to perform one or more processing operations according to a plurality of selectable ultrasound modalities on the acquired ultrasound information. Acquired ultrasound information may be processed and/or displayed in real-time during a scanning session as the echo signals are received. Additionally or alternatively, the ultrasound information may be stored temporarily in the memory 24 during a scanning session and then processed and/or displayed in less than real-time in a live or off-line operation.

The signal processor 26 is connected to a user input device 30 that may control operation of the ultrasound system 10. The user input device 30 may be any suitable device and/or user interface for receiving user inputs to control, for example, the type of scan or type of transducer to be used in a scan. The display system 28 includes one or more monitors that present patient information, including diagnostic ultrasound images to the user for diagnosis and/or analysis. The ultrasound system 10 may include a memory 32 for storing processed frames of acquired ultrasound information that are not scheduled to be displayed immediately. One or both of the memory 24 and the memory 32 may store 3D data sets of the ultrasound data, where such 3D datasets are accessed to present two-dimensional (2D) and/or 3D images. Multiple consecutive 3D datasets may also be acquired and stored over time, such as to provide real-time 3D or 4D display. The images may be modified and/or the display settings of the display system 28 may be manually adjusted using the user input device 30.

In addition to the acoustic elements 12, various other components of the ultrasound system 10 may be considered to be a component of the ultrasound transducer 16. For example, the transmitter 12, the receiver 18, and/or the beamforming electronics 20 may each be a component of the ultrasound transducer 16. In some embodiments, two or more components of the ultrasound system 10 are integrated into an integrated circuit, which may be a component of the ultrasound transducer 16. For example, the transmitter 12, the receiver 18, and/or the beamforming electronics 20 may be integrated into an integrated circuit.

The ultrasound system 10 may include an ultrasound probe 34 that holds one or more various components of the ultrasound transducer 16. For example, as shown in FIG. 1, the ultrasound probe 34 holds the array of acoustic elements 12. In addition to the acoustic elements 12, and for example, the ultrasound probe 34 may hold the transmitter 12, the receiver 18, the beamforming electronics 20, and/or one or more integrated circuits that include any of the components 12, 18, and/or 20.

Figure 7:
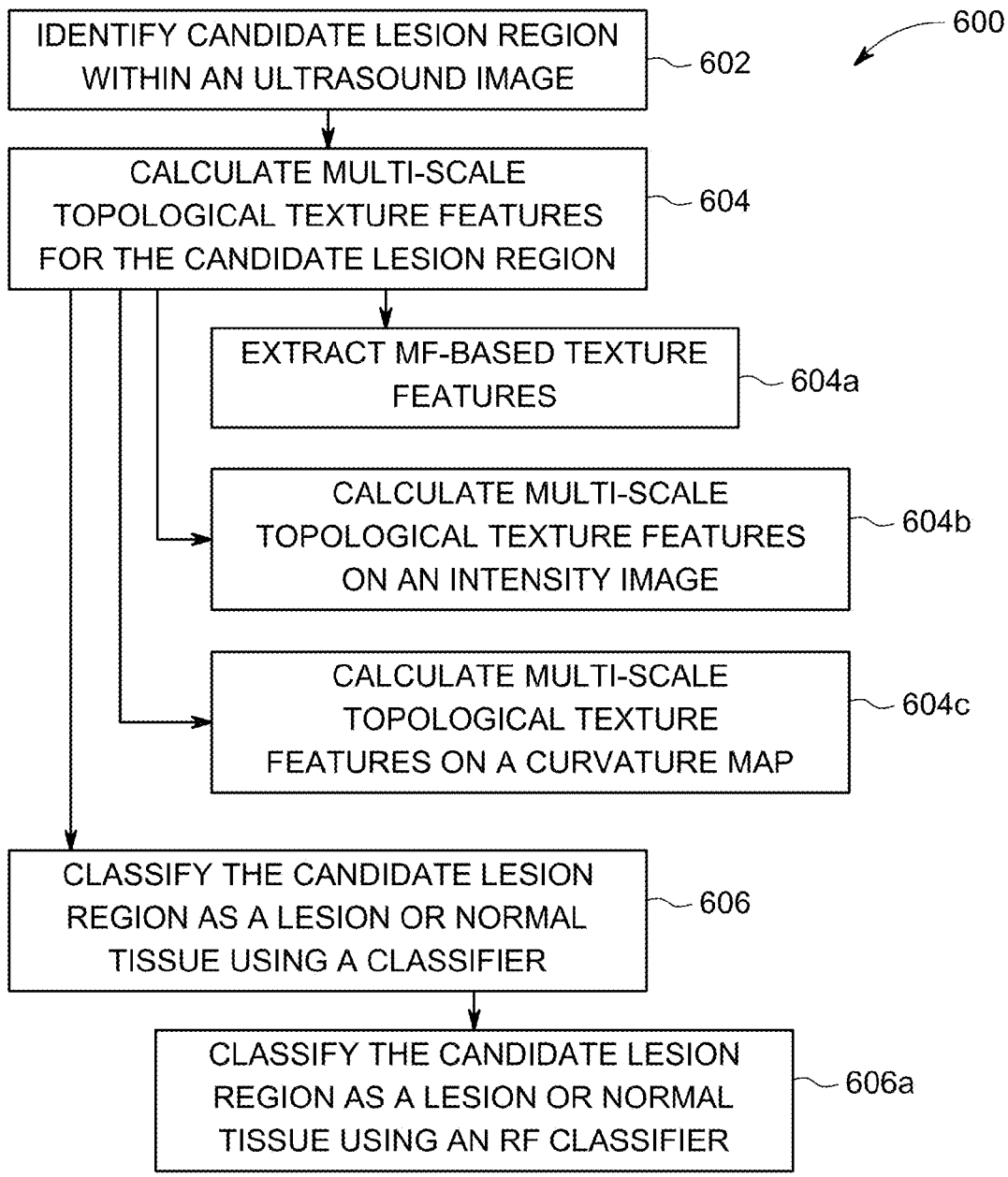
FIG. 7 is a flowchart illustrating a method for detecting lesions in ultrasound images in accordance with various embodiments.
Figure 8:
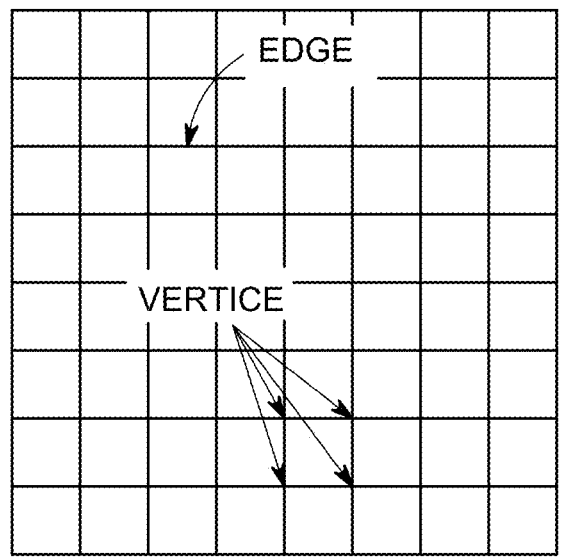
FIG. 8 is a schematic diagram illustrating a lattice representation of a two-dimensional (2D) image for use with the method shown in FIG. 7.
Figure 9:
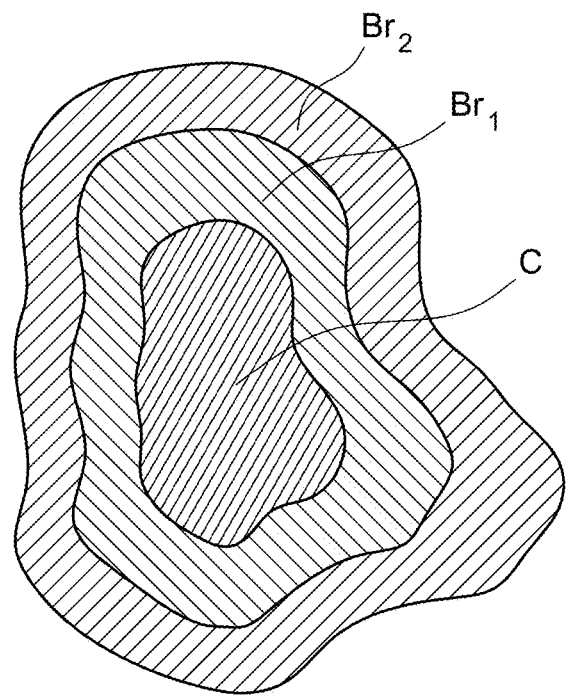
FIG. 9 is a schematic diagram illustrating multi-scale adaptive neighbor regions that may be used in the method shown in FIG. 7.

The ultrasound system 10 may be embodied in a small-sized system, such as, but not limited to, a laptop computer or pocket sized system as well as in a larger console-type system. FIGS. 7 and 8 illustrate small-sized systems, while FIG. 9 illustrates a larger system.

It should be appreciated that although the system 10 is illustrated as a single modality (i.e., ultrasound) imaging system, the various embodiments may be implemented in or with multi-modality imaging systems. For example, the ultrasound system 10 may be combined with different types of medical imaging systems, such as, but not limited to, a Computed Tomography (CT) system, a Positron Emission Tomography (PET) system, a Single Photon Emission Computed Tomography (SPECT) system, a Magnetic Resonance Imaging (MRI) system, and/or any other system capable of generating images.

Figure 2:
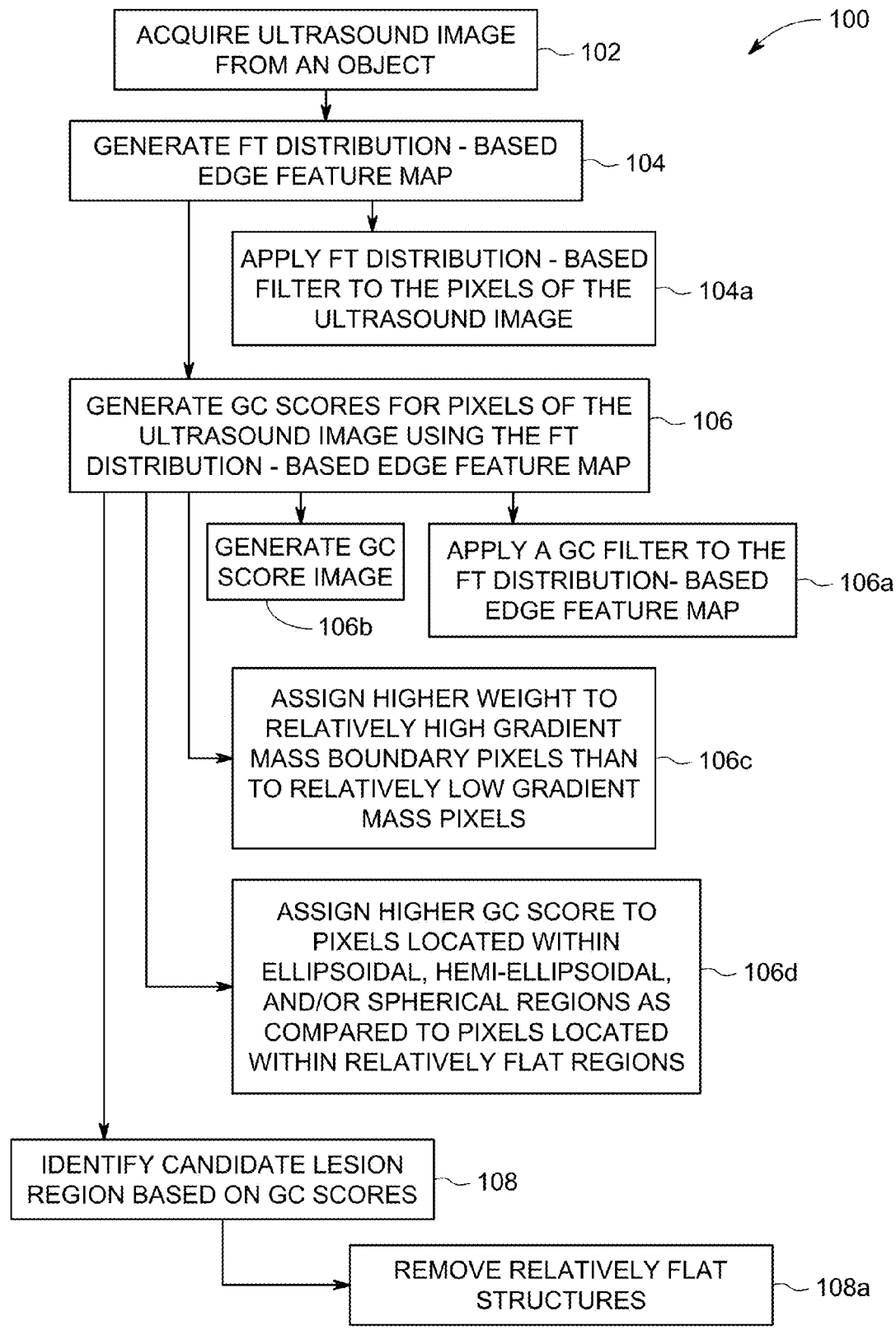
FIG. 2 is a flowchart illustrating a method for detecting lesions in ultrasound images in accordance with various embodiments.

FIG. 2 is a flowchart of a method 100 for detecting lesions in ultrasound images in accordance with various embodiments. It should be noted that although the method 100 is described in connection with ultrasound imaging having particular characteristics, the various embodiments are not limited to ultrasound imaging, nor to any particular imaging characteristics. Rather, the method 100 may be practiced with any imaging modality or any combination of different imaging modalities, such as, but not limited to, CT, PET, SPECT, MRI, and/or the like. For example, the method 100 may be used to detect lesions in other types of images (e.g., CT images, PET images, SPECT images, and/or the like) in addition or alternative to ultrasound images. The method 100 may be particularly meaningful for ultrasound images as the method 100 is configured to consider echoes present at tissue boundaries. The method 100 may be performed, in whole or part, by any suitable imaging system, such as, but not limited to, the ultrasound system 10 (shown in FIG. 1), the ultrasound system 700 (shown in FIG. 13), the ultrasound system 800 (shown in FIG. 14), and/or the ultrasound system 900 (shown in FIG. 15).

At 102, an ultrasound image is acquired from an object. For example, the object may constitute a human breast and the method 100 may be performed for detecting a lesion in the breast to thereby detect breast cancer. But, the object for which the ultrasound image is acquired at 102 is not limited to being a human breast. Rather, the object for which the ultrasound image is acquired at 102 may be any other body part (e.g., organ, tissue, and/or fluid) in a human or other animal, such as, but not limited to, a liver, a bladder, a colon, and/or the like. It should be understood that the method 100 may be used to detect a lesion in any body part of a human or other animal, for example for detecting liver cancer, bladder cancer, colon cancer, and/or the like. The ultrasound image acquired at 102 may include 2D and/or 3D information.

The method 100 uses an FT distribution-based GC filter for identifying candidate lesions. In ultrasound images of the breast, lesions typically appear as a darker region of an ellipsoidal, hemi-ellipsoidal, and/or spherical shape that is surrounded by a brighter background. The FT distribution-based GC filter may be used to remove brighter and relatively high intensity flat regions from the ultrasound image to identify candidate lesion regions within the ultrasound image. The FT distribution-based GC filter of the method 100 includes FT gradient-like feature map calculation and GC calculation. In ultrasound images of the breast, the gradient vector field in the lesion region may be distorted by speckle noise, which may be a fundamental problem in evaluating ultrasound images of the breast.

To suppress the speckle noise, a gradient-like feature map may be generated, for example by applying an FT distribution-based filter to the pixels (also referred to commonly as "voxels") of the ultrasound image. Specifically, the method 100 includes, at 104, generating an FT distribution-based edge feature map from the ultrasound image acquired at 102. In the illustrated embodiment, the FT distribution-based edge feature map is generated at 104 by applying, at 104a, an FT distribution-based filter to the pixels of the ultrasound image. Optionally, applying at 104a the distribution-based filter to the pixels of the ultrasound image includes applying the distribution-based filter to each (i.e., all) of the pixels of the ultrasound image. The FT distribution-based edge feature map generated at 104 constitutes a directional gradient-like edge map that may be robust to noise and/or speckle artifacts presented in the ultrasound image acquired at 102.

An exemplary methodology for generating at 104 the FT distribution-based edge feature map will now be described. Speckle noise may follow an FT distribution:

$$p(I(x,y)) = 2e^{(2I(x,y) - \ln 2\sigma^2 - e^{(2I(x,y) - \ln 2\sigma^2)})}. \quad (1)$$

In a given image region R, the distribution parameter σ is obtained using maximum likelihood estimation:

$$\sigma^2 = \frac{1}{2} \frac{\int_R e^{2I(x,y)} dx\, dy}{\int_R dx\, dy}. \quad (2)$$

Figure 3:
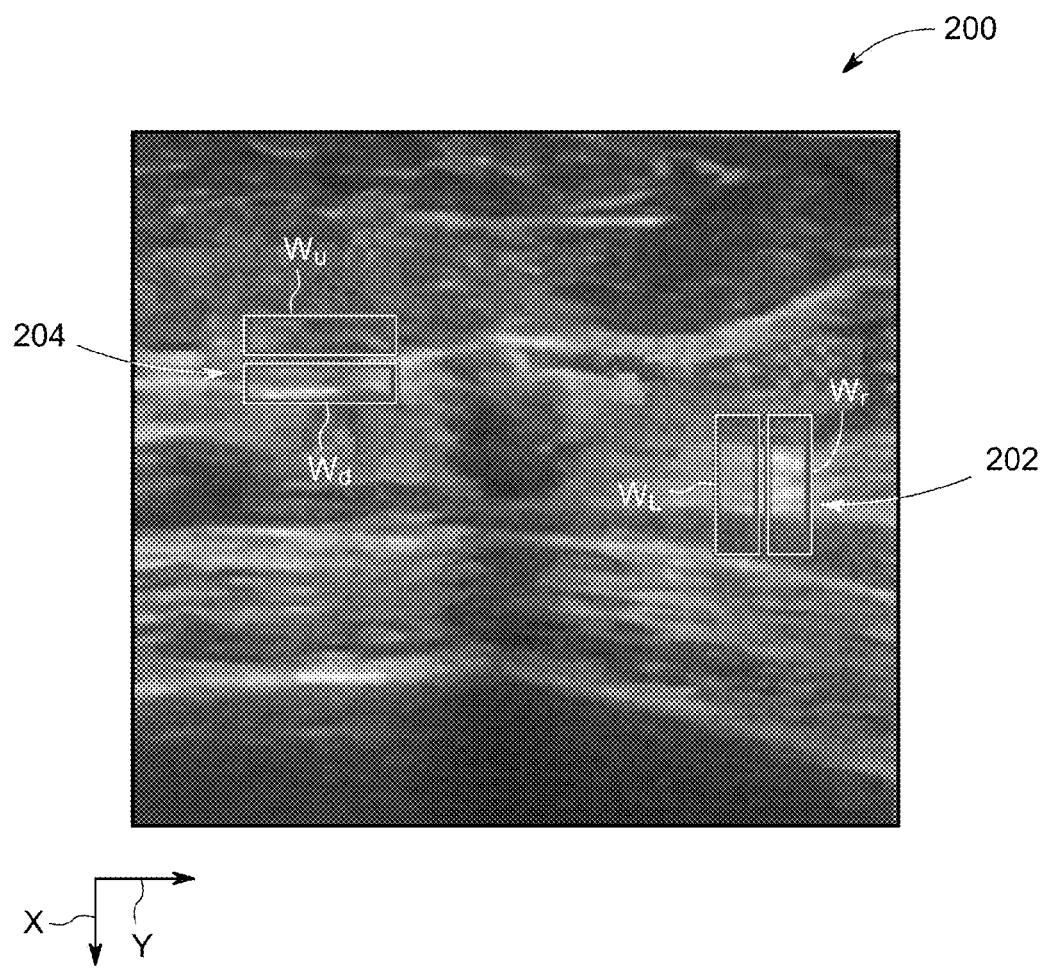
FIG. 3 illustrates an exemplary ultrasound image that has been acquired and partially processed according to the method shown in FIG. 2.

Placing two neighbor regions on the opposite side of a pixel, generating the FT distribution-based edge feature map at 104 includes using J-divergence to measure the distance between the FT distributions of the two neighbor regions. The J-divergence is derived as:

$$J(x,y) = \frac{1}{2} e^{-\frac{1}{2\sigma_1^2}} \left( -\ln 2\sigma_1^2 + \ln 2\sigma_2^2 - 1 - \frac{1}{2\sigma_1^2} + \frac{\sigma_1^2}{\sigma_2^2} + \frac{1}{2\sigma_2^2} \right) + \frac{1}{2} e^{-\frac{1}{2\sigma_2^2}} \left( -\ln 2\sigma_2^2 + \ln 2\sigma_1^2 - 1 - \frac{1}{2\sigma_2^2} + \frac{\sigma_2^2}{\sigma_1^2} + \frac{1}{2\sigma_1^2} \right), \quad (3)$$

where $\sigma_1^2$ and $\sigma_2^2$ are the FT parameters in the two different neighboring regions. Placing two pairs of sliding windows $(W_l, W_r)$ and $(W_u, W_d)$ along the x direction and the y direction, respectively, the gradient-like feature can be calculated as:

$$g(x,y) = (I_{w_r} - I_{w_l}) J_x(x,y) \hat{x} + (I_{w_u} - I_{w_d}) J_y(x,y) \hat{y}, \quad (4)$$

where $J_x(x,y)$ and $J_y(x,y)$ represent the J-divergence along the x and y directions, respectively. FIG. 3 illustrates an exemplary ultrasound image 200 that includes two pairs 202 and 204 of sliding windows $(W_l, W_r)$ and $(W_u, W_d)$, respectively. As can be seen in FIG. 3, the pair of sliding windows $(W_u, W_d)$ is positioned along the y direction, and the pair of sliding windows $(W_l, W_r)$ is positioned along the x direction. The direction of the gradient-feature can be determined by the mean intensity difference between any two of the sliding windows $W_l, W_r, W_u,$ and $W_d$.

At 106, the method 100 includes generating GC scores for the pixels of the ultrasound image acquired at 102 using the FT distribution-based edge feature map generated at 102. Optionally, generating at 106 GC scores for the pixels of the ultrasound image includes generating a GC score for each (i.e., all) of the pixel of the ultrasound image acquired at 102. In the illustrated embodiment, the GC scores are generated at 106 by applying, at 106a, a GC filter to the FT distribution-based edge feature map generated at 104. Generating at 106 the GC scores may include generating, at 106b, a GC score image, for example by applying at 106a the GC filer to the FT distribution-based edge feature map generated at 104.

Figure 4:
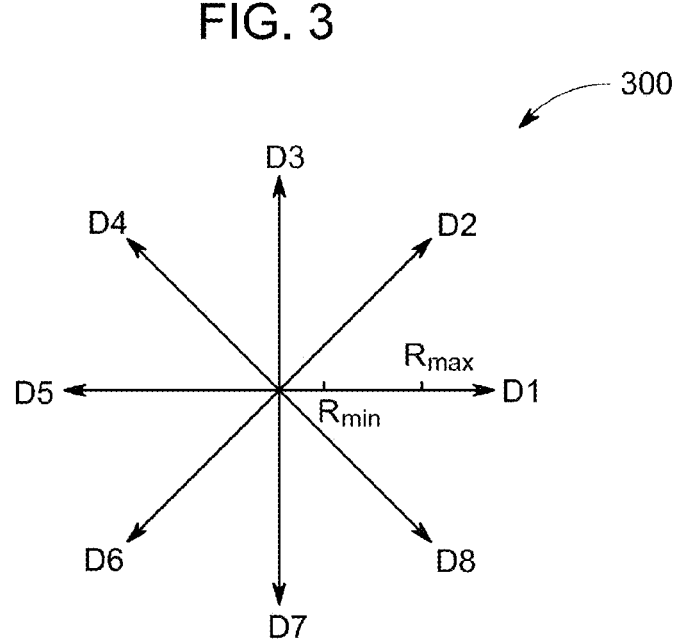
FIG. 4 is a schematic diagram illustrating eight symmetric directions used for gradient concentration (GC) of the method shown in FIG. 2.

An exemplary methodology for generating at 106 the GC scores will now be described. A GC score image may be obtained by applying a GC filter on the directional gradient-like feature image (i.e., the FT distribution-based edge feature map generated at 104) using:

$$GC(x, y) = \frac{1}{\sum_{i=1}^{N} |g_i^{max}|} \sum_{i=1}^{N} <g_i^{max}, u_i>, \quad (5)$$

Where N is the number of symmetric directions, $g_i^{max}$ is the maximum gradient vector along direction i in the distance range [$R_m$in, $R_m$ax], and $\hat{u}_i$ is the unit radial vector along direction i, as is shown in FIG. 4. Specifically, FIG. 4 is a schematic diagram 300 illustrating eight symmetric directions used for generating at 106 the GC score for a pixel. The selection $g_i^{max}$ along each direction in [$R_m$in, $R_m$ax] gives relatively high gradient mass boundary pixels higher weights in the GC computation than relatively low gradient noise pixels. Accordingly, generating at 106 the GC scores may include assigning, at 106c, a higher weight to relatively high gradient mass (i.e., lesion) boundary pixels than to relatively low gradient noise pixels. The value of GC is bounded by [−1,1]. Because a lesion will typically have an ellipsoidal, hemi-ellipsoidal, and/or spherical shape in an ultrasound image of the breast, the GC scores for pixels inside the lesion region will be higher than GC scores for pixels in the surrounding regions with relatively flat-shaped structures. Accordingly, generating at 106 the GC scores may include assigning at 106d, a higher GC score to pixels located within ellipsoidal, hemi-ellipsoidal, spherical regions of the ultrasound image acquired at 102 as compared to pixels located within a relatively flat regions of the ultrasound image. In other words, pixels located inside relatively dark spherical, ellipsoidal, and/or hemi-ellipsoidal regions may be highlighted with a higher GC score.

At 108, the method 100 includes identifying a candidate lesion region within the ultrasound image acquired at 102 based on the GC scores generated at 106. For example, identifying at 108 a candidate lesion region based on the GC scores generated at 106 may include removing, at 108a, relatively flat tissue from the ultrasound image (e.g., from the GC score image) using the GC scores. Removing at 108a the relatively flat tissue from the ultrasound image will expose candidate lesion regions within the ultrasound image and thereby enable the identification at 108. As described above, relatively flat structures will have a lower GC score than ellipsoidal, hemi-ellipsoidal, and/or spherical shaped structures. Removing at 108a the relatively flat tissue from the ultrasound image using the GC scores therefore may include comparing the various GC scores to distinguish relatively flat structures from ellipsoidal, hemi-ellipsoidal, and/or spherical shaped structures.

One example of removing identifying at 108 the candidate lesion region based on the GC scores includes: (1) removing pixels from the GC image that have a GC score lower than a first predetermined threshold; (2) grouping remaining pixels within the GC image that are connected together into grouped components; (3) calculating an average GC score for the grouped components; and (4) removing grouped components with averaged GC scores lower than a second predetermined threshold. The first and/or second thresholds are optionally chosen based on a free-response receiver operating characteristic (FROC) curve (e.g., the FROC curve 500 shown in FIG. 6). It should be understood that identifying at 108 a candidate lesion region does not focus on achieving a precise segmentation of breast mass, but rather facilitates producing a dependable region that covers the real mass region relatively closely.

The output of the method 100 may be used in conjunction with more computationally expensive lesion detection methods such as, but not limited to, a texture-based analysis, a machine learning method, and/or the like. For example, the candidate lesion regions identified at 108 may be fed into other more computationally expensive lesion detection methods, for example to reduce the overall computation time of such methods. In other words, the candidate lesion regions identified at 108 may be used as a pre-processing step to narrow down the lesion searching space and thereby reduce the computational time and effort for later steps (e.g., of such other more computationally expensive lesion detection methods).

Figure 5:
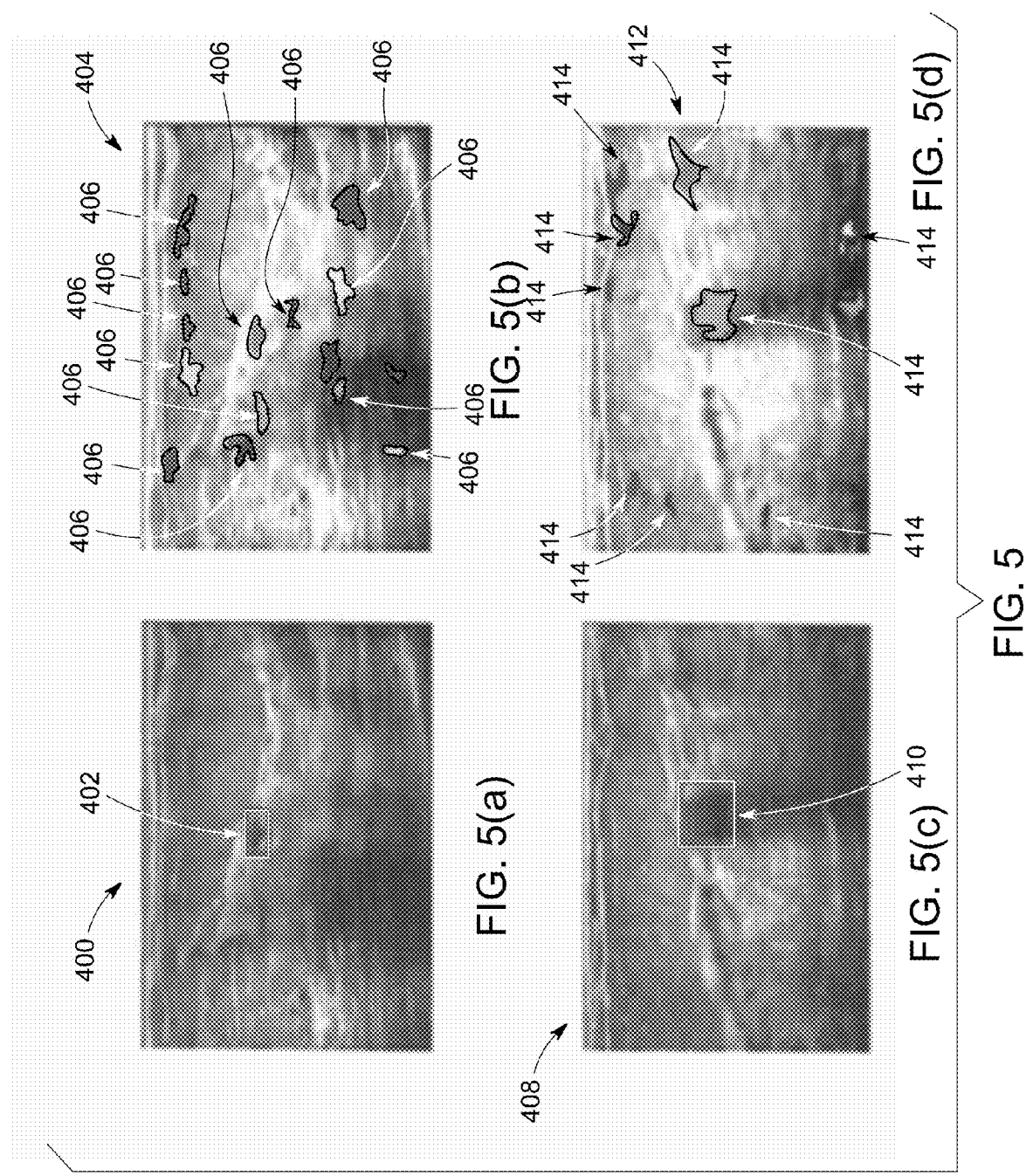
FIG. 5 illustrates exemplary ultrasound images from an experimental evaluation of the method shown in FIG. 2.

Referring now to FIG. 5, the lesion detection methodology of the embodiments described and/or illustrated herein (e.g., the method 100 shown in FIG. 2) was experimentally evaluated on 135 ultrasound images of the breast. The ultrasound images were obtained on using a GE LOGIQ E9 scanner with a 15 MHz linear probe. 139 suspicious lesion regions were manually labeled by a radiologist. Qualitative detection results on a benign tumor and a malignant lesion are shown in FIG. 5. Specifically, FIG. 5(a) illustrates an original (e.g., directly after the acquisition step 102 shown in FIG. 2) ultrasound image 400 of the breast with a manually labeled bounding box 402 around a benign tumor. FIG. 5(b) illustrates the results of the lesion detection methodology described and/or illustrated herein. Specifically, FIG. 5(b) illustrates an ultrasound image 404 after the candidate lesion region identification step 108 (shown in FIG. 2). A plurality of candidate lesion regions 406 have been identified and labeled on the ultrasound image 404. FIGS. 5(a) and 5(b) illustrate that the FT-based GC filter of the embodiments described and/or illustrated herein may efficiently remove the majority of normal tissue regions with relatively flat structures.

FIG. 5(c) illustrates an original (e.g., directly after the acquisition step 102 shown in FIG. 2) ultrasound image 408 of the breast with a manually labeled bounding box 410 around a malignant lesion with posterior acoustic shadowing. FIG. 5(d) illustrates the results of the lesion detection methodology described and/or illustrated herein. Specifically, FIG. 5(d) illustrates an ultrasound image 412 after the candidate lesion region identification step 108 (shown in FIG. 2). A plurality of candidate lesion regions 414 have been identified and labeled on the ultrasound image 412. FIGS. 5(c) and 5(d) illustrate that the FT-based GC filter of the embodiments described and/or illustrated herein may efficiently remove the majority of normal tissue regions with relatively flat structures. Moreover, as can be seen from a comparison of FIGS. 5(a) and 5(b) with FIGS. 5(c) and 5(d), the relatively large size difference between the benign tumor of FIGS. 5(a) and 5(b) and malignant lesion of FIGS. 5(c) and 5(d) illustrate that the FT-based GC filter of the embodiments described and/or illustrated herein may be robust to relatively large lesion size variations.

Figure 6:
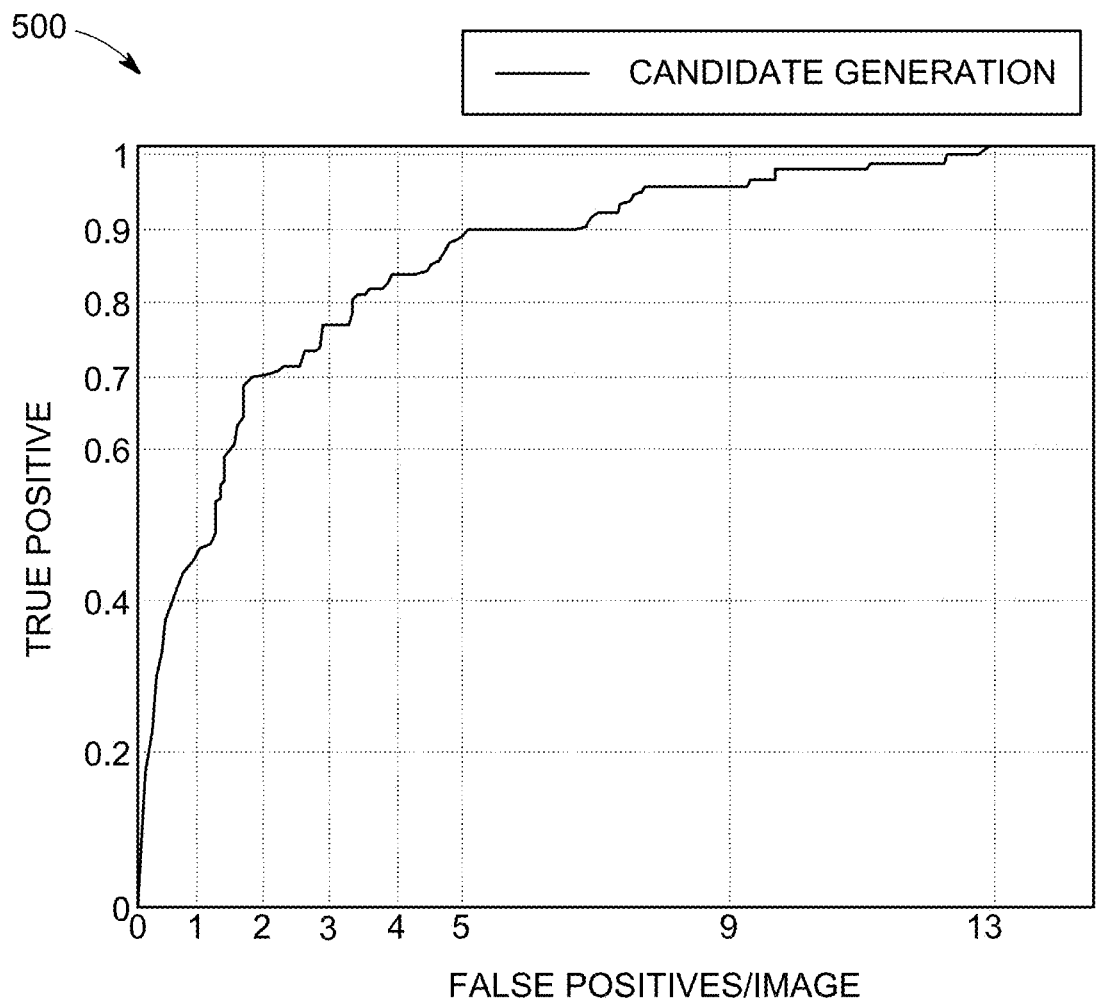
FIG. 6 illustrates results of the experimental evaluation of the method shown in FIG. 2.

Quantitative detection performance of the lesion detection methodology described and/or illustrated herein was tested using FROC analysis. A lesion was counted as detected if a bounding box of a manually labeled lesion has any overlapping regions with a bounding box of a CAD. All detection regions that did not meet the overlapping criterion were counted as false positives. For identification of candidate lesion regions, the averaged GC score on each candidate lesion region was used as the threshold parameter to generate the FROC curve. The corresponding FROC curve 500 is shown in FIG. 6. As illustrated in FIG. 6, the identification of the candidate lesion region step (e.g., the identification step 108 shown in FIG. 2) reached a sensitivity of approximately 100% with an average of 12 false detections per image. As can also be seen in FIG. 6, over 90% of the normal tissue regions of an ultrasound image were removed using the FT-based GC filter methodology described and/or illustrated herein (e.g., the method 100 shown in FIG. 2).

Although the experimental results of FIG. 5 were performed on a 2D ultrasound image, the lesion detection methodology of the embodiments described and/or illustrated herein (e.g., the method 100 shown in FIG. 2) may be performed on 3D or 4D ultrasound data.

The lesion detection methodology of the embodiments described and/or illustrated herein (i.e., the FT distribution-based GC filter described and/or illustrated herein) may be relatively robust to speckle noise. For example, the lesion detection methodology of the embodiments described and/or illustrated herein may be more robust to speckle noise as compared to at least some known lesion detection methodologies. The lesion detection methodology of the embodiments described and/or illustrated herein may be suitable for identifying candidate lesion regions in a CAD system to detect ellipsoidal, hemi-ellipsoidal, and/or spherical shaped structures. The lesion detection methodology of the embodiments described and/or illustrated herein may be configured to reduce over 90% normal tissue pixels in an image with approximately 100% sensitivity and relatively low false detections. Moreover, as described above, the lesion detection methodology of the embodiments described and/or illustrated herein may reduce overall CAD computation time by being used as a pre-processing step for other more computational expensive lesion detection methods.

At least some known lesion detection methodologies use traditional smoothing filters (e.g., Gaussian filters, median filters, and/or the like) as pre-processing steps to smooth an ultrasound image, and thereafter compute the gradient on the smoothed image. But, the smoothing process may blur that boundary of a lesion, which may make the lesion more difficult to detect. Moreover, the smoothing of the ultrasound image smoothes out detailed local texture information inside the lesion. Such local texture information may be useful within a texture-based lesion detection methodology.

The lesion detection methodology of the embodiments described and/or illustrated herein (i.e., the FT distribution-based GC filter described and/or illustrated herein) skips the smoothing step of at least some known lesion detection methodologies and may calculate a noise robust directional gradient-like feature for each pixel directly and use the directional gradient-like feature to calculate GC scores for each pixel. The GC score may be more robust to speckle noise than known lesion detection methodologies that include smoothing filters. Moreover, without explicitly applying smoothing filters, the lesion detection methodology of the embodiments described and/or illustrated herein preserves the local texture information, which may enable the lesion detection methodology of the embodiments described and/or illustrated herein to be used as a pre-processing step for a texture-based detection methodology.

For example, FIG. 7 is a flowchart of a method 600 for detecting lesions in ultrasound images in accordance with various embodiments. The method 600 is a texture-based detection methodology that may be used with the lesion detection methodology described above with respect to the method 100 of FIG. 2. It should be noted that although the method 600 is described in connection with ultrasound imaging having particular characteristics, the various embodiments are not limited to ultrasound imaging, nor to any particular imaging characteristics. Rather, the method 600 may be practiced with any imaging modality or any combination of different imaging modalities, such as, but not limited to, CT, PET, SPECT, MRI, and/or the like. For example, the method 600 may be used to detect lesions in other types of images (e.g., CT images, PET images, SPECT images, and/or the like) in addition or alternative to ultrasound images. The method 600 may be particularly meaningful for ultrasound images as the method 600 is configured to consider echoes present at tissue boundaries. The method 600 may be performed, in whole or part, by any suitable imaging system, such as, but not limited to, the ultrasound system 10 (shown in FIG. 1), the ultrasound system 700 (shown in FIG. 13), the ultrasound system 800 (shown in FIG. 14), and/or the ultrasound system 900 (shown in FIG. 15).

Given a normalized image and one or more candidate lesion regions with an irregular shape, as will be described below the method 600 may include adaptively calculating multi-scale topological texture features (e.g., derived from Minkowski Functional (MF)) for the candidate lesion region(s), and the method 600 may include using a classifier (e.g., a relatively fast Random Forests (RF) classifier) to classify the candidate lesion region(s) as a lesion or normal tissue (e.g., normal background tissue).

Texture, morphological, and geometrical features are three important types of discriminative features for mass detection. MF, defined in integral geometry, is a family of morphological descriptors that characterize not only texture content but also topology and shape of spatial patterns. An introduction to MF and the computation of three MFs in 2D images will now be described. Given a convex set K in the d-dimension Euclidean space $R^N$, the parallel convex set $K_r$ is defined as the union of all closed balls b(k, r) of radius r centered at the point $$k \in K: K_r = \bigcup_{k \in K} b(k, r)$$

The definition of MFs is given by the Steiner formula:

$$V(K_r) = \sum_{i=0}^{d} \binom{d}{i} W_i(K) r^i, \qquad (6)$$

where V is the volume, $W_i(K)$ is the MFs for K. For computation simplicity, normalized MFs are used:

$$M_i(K) = \frac{w_{d-1}}{w_d w_i} W_i(K), \qquad (7)$$

where $\omega_d$ is the volume of the unit ball in d dimensions ($\omega_1=1$, $\omega_2=\pi$, and $\omega_3=4\pi/3$). In a 2D image, the MFs correspond to simple geometrical quantities: area $M_0(K)=A(k)$, boundary length $$M_1(K) = \frac{1}{2\pi} L(K)$$

and Euler characteristic (number of connected components minus number of $$M_2(K) = \frac{1}{\pi}\chi(K).$$

holes)

MFs could be further generalized from a single convex set to a finite union of convex sets named convex ring:

$$R = \bigcup_{i=1}^{I} K_i.$$

Given the additive nature of MFs:

$$M_i(K_1 \cup K_2) = M_i(K_1) + M_i(K_2) - M_i(K1 \cap K2),$$

MFs for convex ring could be calculated as:

$$M_i(R) = \qquad\qquad\qquad\qquad\qquad\qquad (9)$$

$$\sum_{i=1}^{L} M_i(K) - \sum_{l<j} M_i(K_l \cap K_j) + \ldots + (-1)^{(L+1)} M_i(K1 \cap \ldots \cap K_L)$$

Hadwiger's characterization theorem establishes that in dimension d, every motion-invariant additive continuous functional can be represented by a linear combination of the d+1 MFs. MFs therefore form a complete system of morphological measures on the convex ring. In other words, the set of all rotation-invariant, additive, continuous texture features is fully represented by MFs.

Given a 2D grey-scale image I and a threshold $\rho$, we define the excursion set $I(\rho)$ at threshold $\rho$ as the union of all pixels with intensity value greater than $\rho$. Because each pixel in 2D is a convex set, the excursion set could be considered as an instance of the convex ring. Consider each pixel as the center of a square lattice with width as the distance between two adjacent pixels as shown in FIG. 8. (Each square in FIG. 8 represents a pixel located at its center with four edges and four vertices.) The area, length, and Euler characteristic for the intersection of neighbor pixels could be estimated by counting the number of squares, edges, and vertices. Derived from Equation (9), the MFs on an excursion set $I(\rho)$ could be calculated as:

$$M_1(I(\rho)) = N_s, \quad M_2(I(\rho)) = \frac{1}{2\pi}(4N_s - 2N_e), \qquad (10)$$

$$M_3(I(\rho)) = \frac{1}{\pi}(N_s - N_e + N_v),$$

where $N_s$, $N_e$, and $N_v$ are the number of squares, edges, and vertices, respectively, in $I(\rho)$.

At 602, a candidate lesion region is identified within an ultrasound image. The candidate lesion region may be identified at 602 using any suitable method, process, and/or the like, such as, but not limited to, using the lesion detection method 100 shown in FIG. 2.

At 604, the method 600 includes calculating multi-scale topological texture features for the candidate lesion region. The multi-scale topological texture features calculated at 604 may be derived from MF such that calculating at 604 the multi-scale topological texture features for the candidate lesion region includes extracting, at 604a, MF-based texture features for the candidate lesion region.

The most common known way to extract MF-based features is to assign a square region of interest (ROI) around each pixel and use MFs on the ROI as a feature vector for the center pixel. But, there are two problems for using ROI with the method 600: (1) the ROI cannot properly model the local texture for mass with irregular shapes, especially for pixels located at the boundary of mass; and (2) the computation complexity for calculating MFs on each pixel could be relatively very high. To solve such problems, the method 600 extracts MF-based features in an adaptive multi-scale manner for each candidate lesion region. Given a candidate lesion region with an arbitrary (e.g., irregular) shaped region C (e.g., produced using a pre-processing step such as the method 100 shown in FIG. 2 and/or Otsu threshold), the method 600 extracts at 604a the MF-based features on C by sweeping the threshold $\rho$ through all intensity levels and calculating MFs $M_i(C(\rho))$ on each excursion set $C(\rho)$. Such MFs obtained at different thresholds illustrate how the topological structure changes at different intensity levels, and describes the local texture, shape, and topology properties inside the candidate mass. To consider (i.e., include) the tissue structure around the mass border, a narrow band region B around each candidate region C is also extracted: $B_{r1} = C_{r1} - C$, where $C_{r1}$ is the parallel set of C with radius $r_1$. MFs $M_i(B_{r1}(\rho))$ on the band region are generated as background region features. To capture background information for masses with different sizes, the method 600 may extract at 604a more than one band region for each candidate lesion region in a multi-scale manner with different radii as shown in FIG. 9. At last, the three MFs calculated at P thresholds and Q band regions are concatenated into one P×(Q+1) dimensional feature vector for the candidate lesion region. Accordingly, calculating at 604 multi-scale topological texture features for the candidate lesion region comprises calculating at 604b the multi-scale topological texture features (i.e., the MF-based topological texture features) on an intensity image.

Although MFs on an intensity image provide shape information implicitly by measuring area and length change at different intensity levels, additional (e.g., more accurate) shape information could be obtained by computing the MFs explicitly on a curvature map (e.g., a 2D curvature image). The curvature of the intensity isocountour passing through a pixel could characterize the local shapes of the relevant (i.e., corresponding) anatomical structures, and can be computed directly from the curvature tensor on each pixel. The method step of 604 may include computing curvature on each pixel to produce a curvature image, and then applying the same feature extraction procedure (i.e., the method step of 604a) on the curvature image to produce features describing the curvature distributions inside and around the mass region. In some embodiments, 10 intensity values evenly divide the normalized intensity range [0, 1] of the images, and 3 different radii are used to create boundary bands for both intensity and curvature images. Each candidate lesion region may be represented by a 240 dimensional feature vector. Accordingly, calculating at 604 multi-scale topological texture features for the candidate lesion region comprises calculating at 604c the multi-scale topological texture features (i.e., the MF-based topological texture features) on a curvature map.

After extracting the topological features from a candidate lesion region, a classifier needs is used to classify the candidate lesion region as normal tissue or as a lesion (i.e., mass) region. Accordingly, the method 600 includes classifying, at 606, the candidate lesion region as a lesion or normal tissue using a classifier. In the illustrated embodiment, a non-linear Random Forests (RF) classifier is used to classify at 606 the candidate lesion region as a lesion or normal tissue. Classifying at 606 the candidate lesion region as a lesion or normal tissue may therefore include classifying, at 606a, the candidate lesion region as a lesion or normal tissue using an RF classifier. Any other classifier(s) could be used for classifying at 606 in addition or alternatively to an RF classifier.

RF has gained popularity in the computer vision community, because RF may be particularly suitable for non-linear classification with relatively high-dimensional data and relatively noisy data. Considering the noise in breast ultrasound (BUS) data and the relatively high-dimensional MF-based feature vectors used in the method 600, RF has been selected as the classifier to classify each candidate lesion region as normal tissue or a lesion. An RF classifier is a collection of decision trees whose decisions are combined to make the overall decision for the forest. To construct a forest with N trees, for each tree, M training samples are randomly selected from the original training data set, in the tree growing stage, at each decision node, P features are randomly used to split the tree. During testing stage, each tree will give a vote to the classification. The final classification is the weighted sum of the vote of all trees. In some embodiments, the RF classifier is built from 100 trees, 60% of the training data is used to build each tree, and randomly selected features are used at each node. The testing result for each candidate lesion region may be a voting score in [1, 100].

Figures 10, 10A, 10B:
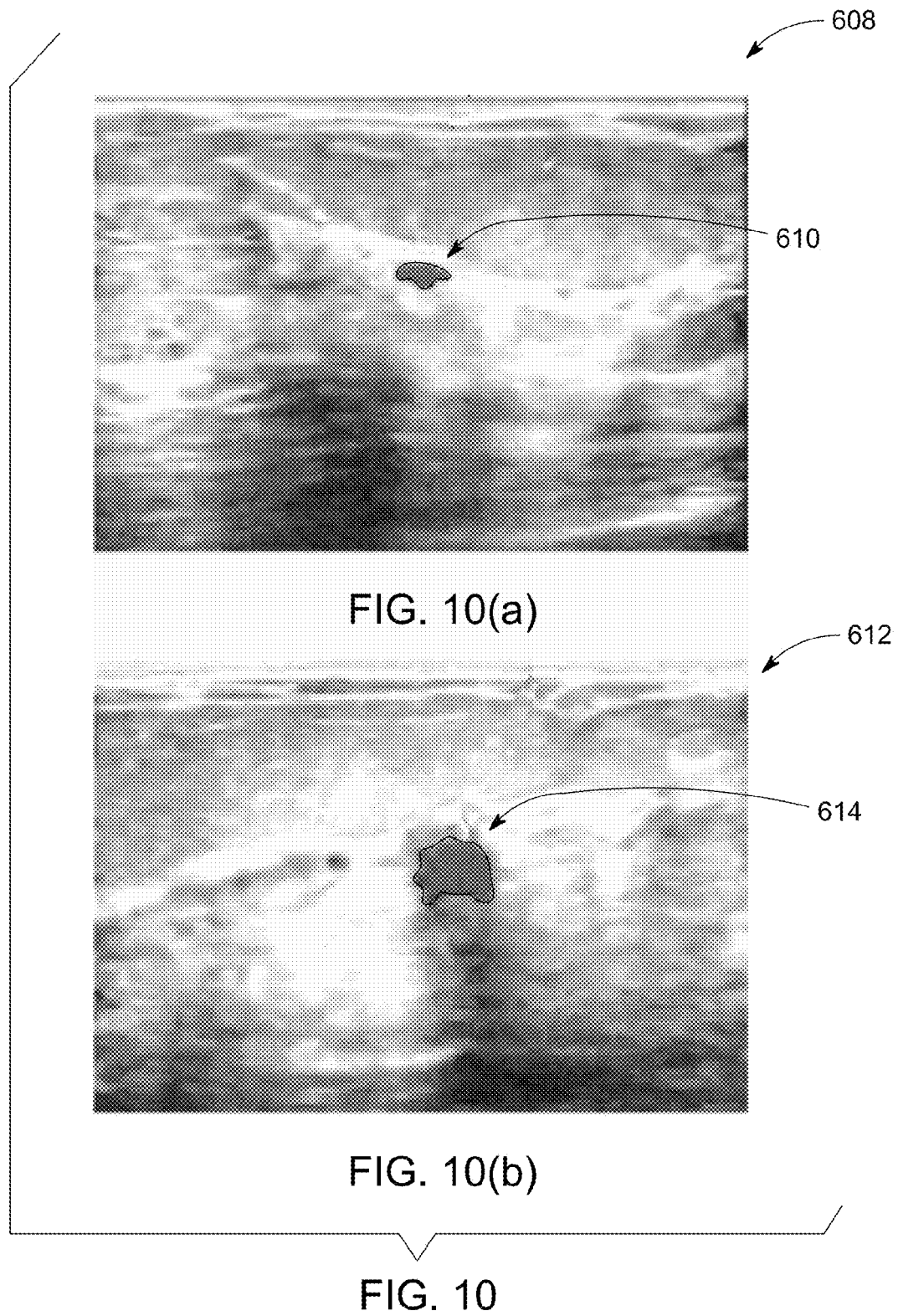
FIG. 10 illustrates exemplary ultrasound images from an experimental evaluation of the method shown in FIG. 7.

Referring now to FIG. 10, the lesion detection methodology of the embodiments described and/or illustrated herein (e.g., the method 600 shown in FIG. 7) was experimentally evaluated on 135 ultrasound images of the breast. The ultrasound images were obtained on using a GE LOGIQ E9 scanner with a 15 MHz linear probe. 139 suspicious lesion regions were manually labeled by a radiologist. Because the CAD is developed to reduce radiologists' reading burden during screening, the experimental evaluation focused on mass (i.e., lesion; including benign and malignant lesions) detection instead of mass characterization (i.e., diagnosis). No biopsy reference was used in the experimental results.

Qualitative detection results on a benign tumor and a malignant lesion are shown in FIG. 10. Specifically, FIG. 10(a) illustrates the results of the lesion detection methodology of the method 600 of FIG. 7 on the benign tumor. Specifically, FIG. 10(a) illustrates an ultrasound image 608 after the classification step 606 (shown in FIG. 7). All false detections produced in the identification (e.g., the identification step 108 of the method 100 shown in FIG. 2) of the candidate lesion region(s) have been removed while a candidate lesion region has been correctly classified as a lesion 610. For example, only one of the candidate lesion regions 406 shown in FIG. 5(b) has been detected as a lesion 610 in FIG. 10(a).

FIG. 10(b) illustrates the results of the lesion detection methodology of the method 600 of FIG. 7 on the malignant lesion. Specifically, FIG. 10(b) illustrates an ultrasound image 612 after the classification step 606 (shown in FIG. 7). All false detections produced in the identification (e.g., the identification step 108 of the method 100 shown in FIG. 2) of the candidate lesion region(s) have been removed while a candidate lesion region has been correctly classified as a lesion 614. For example, only one of the candidate lesion regions 414 shown in FIG. 5(d) has been detected as a lesion 614 in FIG. 10(b). The lesion 614 displays a pronounced posterior acoustic shadow, often associated with malignant tumors. The false detections (visible in FIG. 5(d) as candidate lesion regions 414) in the posterior acoustic shadow below the lesion 614 have been correctly removed using the multi-scale methods (e.g., the method 600 shown in FIG. 7) of the embodiments described and/or illustrated herein.

As can be seen from a comparison of FIGS. 10(a) and 10(b), the relatively large size difference between the benign tumor of FIG. 10(a) and the malignant lesion of FIG. 10(b) illustrate that the multi-scale methods (e.g., the method 600 shown in FIG. 7) of the embodiments described and/or illustrated herein may be robust to relatively large lesion size variations.

The topological feature-based classification method 600 of FIG. 7 was compared with a less computation expensive GC candidate generation method and with grey level co-occurrence matrix (GLCM). For each candidate lesion region, co-occurrence matrices with four directions ($0°$, $45°$, $90°$, and $135°$) and three distances (1, 2, 3) were computed. Five kinds of GLCM-based texture descriptors (energy, entropy, contrast, cluster shade, and correlation) derived from co-occurrence matrices were used as texture features.

Figure 11:
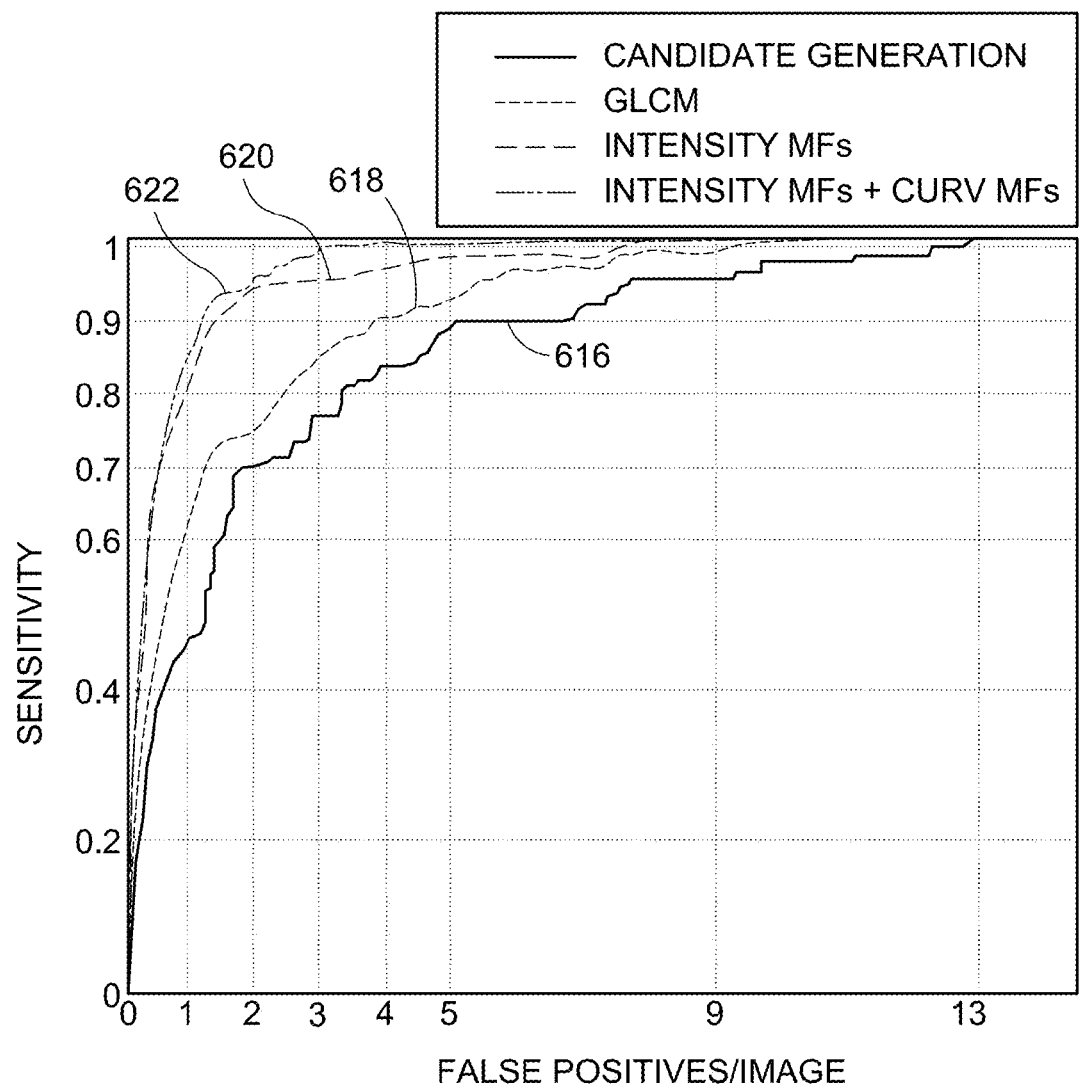
FIG. 11 illustrates results of the experimental evaluation of the method shown in FIG. 7.

Quantitative detection performance of the compared methods was tested using FROC analysis. A lesion was counted as detected if: 1) the CAD detection region overlapped with the manually labeled bounding box; and 2) the center point of the detection is inside the manually labeled bounding box. All detection regions that did not meet this criterion were counted as false positives. The detection results were evaluated for both the candidate lesion region identification step (i.e., stage) and the classification step using: 1) GLCB-based features; 2) a topological feature-based classification method that uses MF-based features on intensity image only; 3) and a topological feature-based classification method that uses MF-based features on both intensity image and curvature image. For candidate generation, the averaged GC score on each candidate lesion region was used as the threshold parameter to generate the FROC curve. For RF classification, the voting score was used as the threshold parameter to generate the FROC curve. Ten-fold cross-validation was used to evaluate the classification results. The corresponding FROC curves are shown in FIG. 11. Specifically, FIG. 11 includes a FROC curve 616 of an FT-based GC candidate generation method, a FROC curve 618 that classified using GLCM, a FROC curve 620 that classified using a topological feature-based classification method that uses MF-based features on intensity image only, and a FROC curve 622 that classified using a topological feature-based classification method that uses MF-based features on both intensity image and curvature image. FIG. 12 is a table illustrating sensitivity versus false detections for the four methods of FIG. 11 at three selected FROC operating points with sensitivity of 91%, 97%, and 99%.

As can be seen in FIGS. 11 and 12, the GC candidate generation method reached a sensitivity of 91% with an average 6.8 false detections per image. Maintaining the same sensitivity level of 91%, the GLCM-based approach has 4.16 false positives per image, while the intensity-only MF feature-based RF classifications reduced the number of false detections per image to approximately 1.3 per image and the intensity and curvature MF feature-based RF classifications reduced the number of false detections to 1.19 false detections per image. In other words, the intensity and curvature MF feature-based RF classification yielded 71% fewer false detections as compared to the GLCM-based method, while maintaining the same 91% sensitivity.

Although the experimental results of FIGS. 10-12 were performed on a 2D ultrasound image, the lesion detection methodology of the embodiments described and/or illustrated herein (e.g., the method 600 shown in FIG. 7) may be performed on 3D or 4D ultrasound data.

The lesion detection methodology of the method 600 of FIG. 7 applies RF for lesion detection in ultrasound images (e.g., breast ultrasound images). Unlike known methods for lesion detection that extract texture, morphological, and geometrical topological features separately, the multi-scale methods (e.g., the method 600 shown in FIG. 7) of the embodiments described and/or illustrated herein can characterize texture, morphological, and geometrical topological features for a given candidate lesion region at the same time (i.e., simultaneously). Additionally, the calculation of MFs on curvature maps may provide more information of local structure (e.g., shape information) as compared to at least some known methods, which may further improve detection accuracy. Moreover, calculating MF's across multiple scales on adaptive neighbor regions may allow the multi-scale methods (e.g., the method 600 shown in FIG. 7) of the embodiments described and/or illustrated herein to detect lesions with relatively large size variations. The RF classifier may have a relatively high dimensional feature vector as input, which may produce relatively high classification rates even without any feature selection. Given an image and a set of candidate lesion regions with irregular shape, the multi-scale methods (e.g., the method 600 shown in FIG. 7) of the embodiments described and/or illustrated herein can fine tune the candidate lesion region identification results by reducing false detections and maintaining a relatively high sensitivity.

Figure 13:
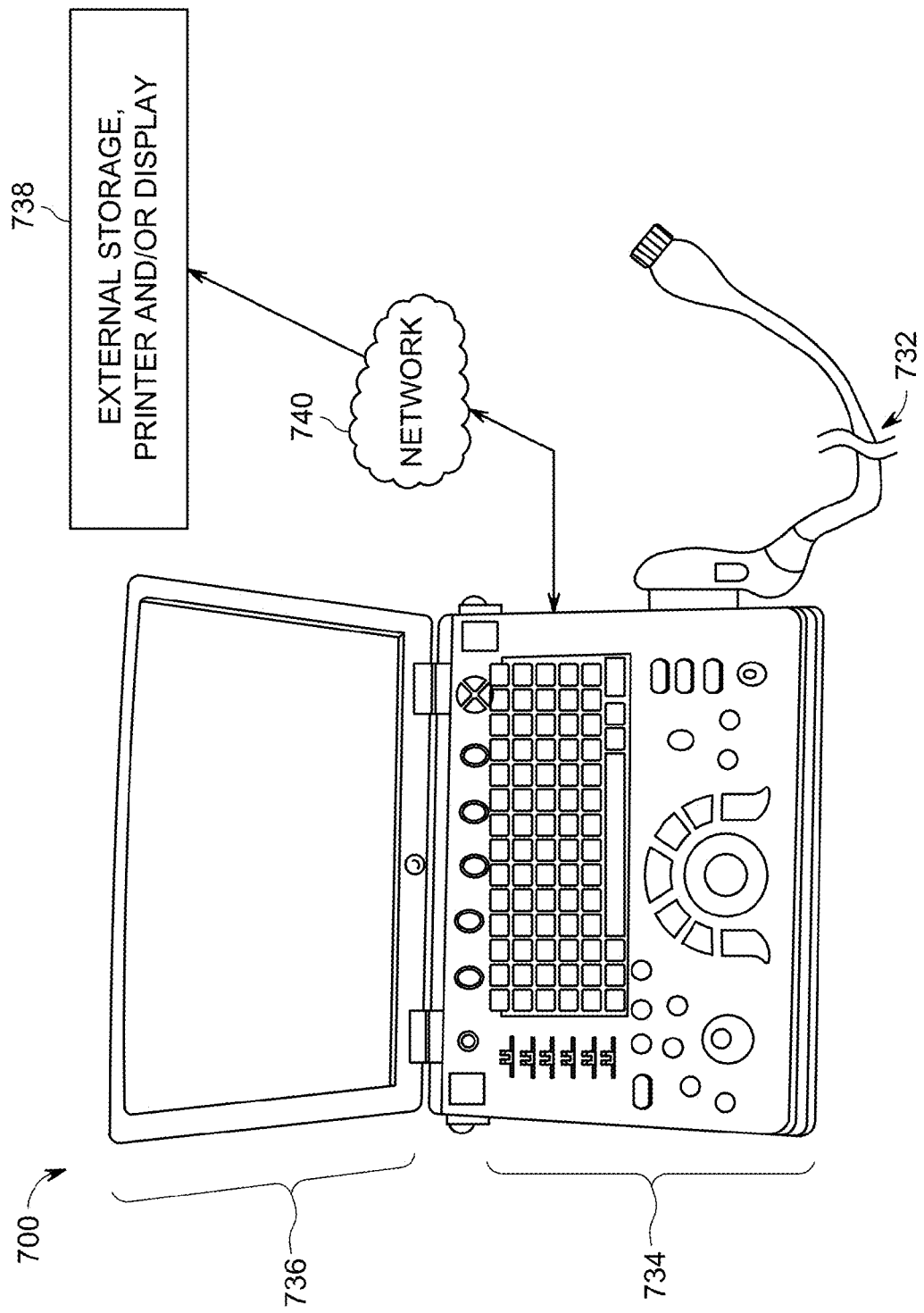
FIG. 13 is a diagram illustrating a three-dimensional (3D) capable miniaturized ultrasound system in which various embodiments may be implemented.

FIG. 13 illustrates a 3D-capable miniaturized ultrasound system 700 having an ultrasound transducer 732 that may be configured to acquire 2D and/or 3D ultrasonic data or multi-plane ultrasonic data. For example, the ultrasound transducer 732 may have a 2D array of acoustic elements. A user interface 734 (that may also include an integrated display 736) is provided to receive commands from an operator. As used herein, "miniaturized" means that the ultrasound system 730 is a handheld or hand-carried device or is configured to be carried in a person's hand, pocket, briefcase-sized case, and/or backpack. For example, the ultrasound system 730 may be a hand-carried device having a size of a typical laptop computer. The ultrasound system 730 is easily portable by the operator. The integrated display 736 (e.g., an internal display) is configured to display, for example, one or more medical images.

The ultrasonic data may be sent to an external device 738 via a wired or wireless network 740 (or direct connection, for example, via a serial or parallel cable or USB port). In some embodiments, the external device 738 may be a computer or a workstation having a display, or the DVR of the various embodiments. Alternatively, the external device 738 may be a separate external display or a printer capable of receiving image data from the hand carried ultrasound system 730 and of displaying or printing images that may have greater resolution than the integrated display 736.

Figure 14:
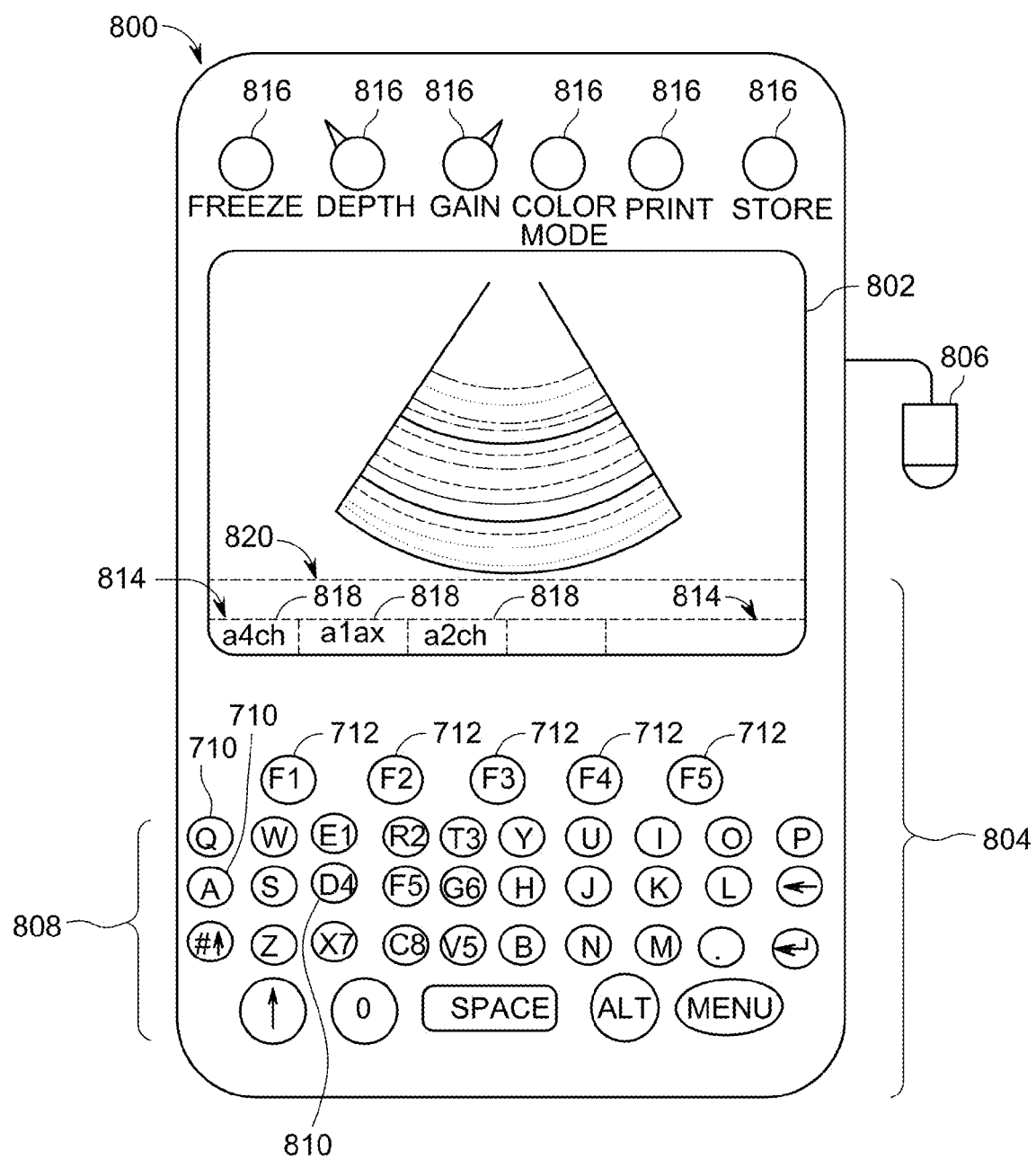
FIG. 14 is a diagram illustrating a 3D capable hand carried or pocket-sized ultrasound imaging system in which various embodiments may be implemented.

FIG. 14 illustrates a hand carried or pocket-sized ultrasound imaging system 800 wherein the display 802 and user interface 804 form a single unit. By way of example, the pocket-sized ultrasound imaging system 800 may be a pocket-sized or hand-sized ultrasound system approximately 2 inches wide, approximately 4 inches in length, and approximately 0.5 inches in depth and weighs less than 3 ounces. The pocket-sized ultrasound imaging system 800 generally includes the display 802, user interface 804, which may or may not include a keyboard-type interface and an input/output (I/O) port for connection to a scanning device, for example, and an ultrasound transducer 806. The display 802 may be, for example, a 320×320 pixel color LCD display (on which a medical image 884 may be displayed). A typewriter-like keyboard 808 of buttons 810 may optionally be included in the user interface 804.

Multi-function controls 812 may each be assigned functions in accordance with the mode of system operation (e.g., displaying different views). Therefore, each of the multi-function controls 812 may be configured to provide a plurality of different actions. Label display areas 814 associated with the multi-function controls 812 may be included as necessary on the display 802. The system 800 may also have additional keys and/or controls 816 for special purpose functions, which may include, but are not limited to "freeze," "depth control," "gain control," "color-mode," "print," and "store."

One or more of the label display areas 814 may include labels 818 to indicate the view being displayed or allow a user to select a different view of the imaged object to display. The selection of different views also may be provided through the associated multi-function control 812. The display 802 may also have a textual display area 820 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 800 and the miniaturized ultrasound system 700 (shown in FIG. 13) may provide the same scanning and processing functionality as the ultrasound system 10 (shown in FIG. 1)

Figure 15:
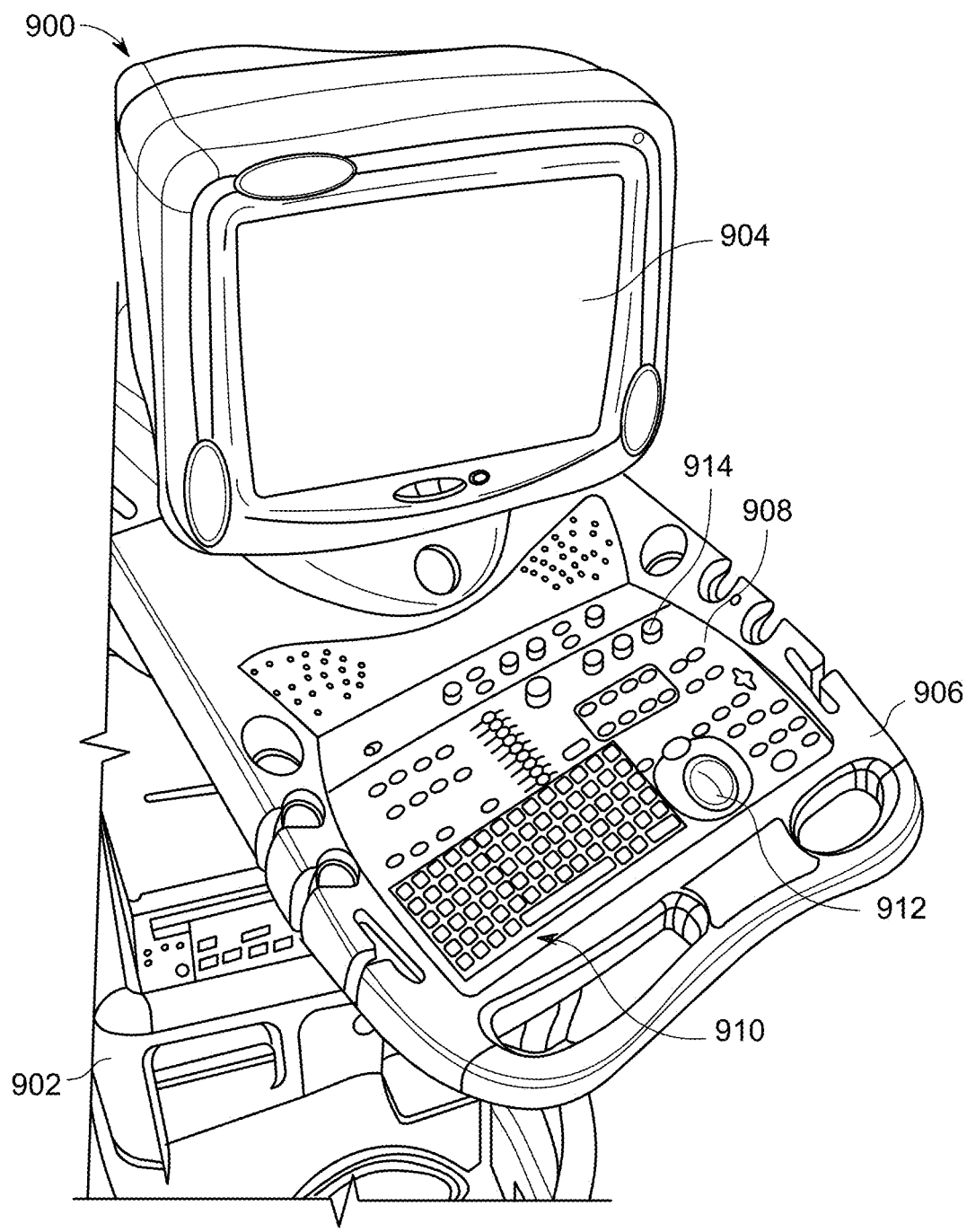
FIG. 15 is a diagram illustrating a 3D capable console type ultrasound imaging system in which various embodiments may be implemented.

FIG. 15 illustrates an ultrasound imaging system 900 provided on a movable base 902. The portable ultrasound imaging system 900 may also be referred to as a cart-based system. A display 904 and user interface 906 are provided and it should be understood that the display 904 may be separate or separable from the user interface 906. The user interface 906 may optionally be a touchscreen, allowing the operator to select options by touching displayed graphics, icons, and/or the like.

The user interface 906 also includes control buttons 908 that may be used to control the portable ultrasound imaging system 900 as desired or needed, and/or as typically provided. The user interface 906 provides multiple interface options that the user may physically manipulate to interact with ultrasound data and other data that may be displayed, as well as to input information and set and change scanning parameters and viewing angles, etc. For example, a keyboard 910, trackball 912, and/or multi-function controls 914 may be provided.

It should be noted that although the various embodiments may be described in connection with an ultrasound system, the methods and systems are not limited to ultrasound imaging or a particular configuration thereof. The various embodiments of ultrasound imaging may be implemented in combination with different types of imaging systems, for example, multi-modality imaging systems having an ultrasound imaging system and one of an x-ray imaging system, magnetic resonance imaging (MRI) system, computed-tomography (CT) imaging system, positron emission tomography (PET) imaging system, among others. Further, the various embodiments may be implemented in non-medical imaging systems, for example, non-destructive testing systems such as ultrasound weld testing systems or airport baggage scanning systems.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and/or the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for detecting lesions in ultrasound images, said method comprising:
acquiring an ultrasound image;
generating a Fisher-tippett (FT) distribution-based edge feature map from the acquired ultrasound image;
generating gradient concentration (GC) scores for pixels of the acquired ultrasound image using the FT distribution-based edge feature map;
identifying a candidate lesion region within the acquired ultrasound image based on the GC scores; and
displaying at least the identified candidate lesion region.

2. The method of claim 1, wherein generating the FT distribution-based edge feature map comprises applying a distribution-based filter to the pixels of the acquired ultrasound image.

3. The method of claim 1, wherein the FT distribution-based edge feature map comprises a directional gradient-like edge map.

4. The method of claim 1, wherein generating the GC scores using the FT distribution-based edge feature map comprises applying a GC filter to the FT distribution-based edge feature map.

5. The method of claim 1, wherein generating the GC scores comprises generating a GC score image.

6. The method of claim 1, wherein generating the GC scores comprises assigning a higher weight to relatively high gradient mass boundary pixels than to relatively low gradient noise pixels.

7. The method of claim 1, wherein generating the GC scores using the FT distribution-based edge feature map comprises assigning a higher GC score to a pixel located within at least one of an ellipsoidal, a hemi-ellipsoidal, or a spherical region of the ultrasound image as compared to a pixel located within a relatively flat region of the ultrasound image.

8. The method of claim 1, wherein generating the GC scores comprises generating a GC score image, and wherein identifying a candidate lesion region within the acquired ultrasound image based on the GC scores comprises removing relatively flat tissue from the GC score image.

9. The method of claim 1, wherein generating the GC scores comprises generating a GC score image, and wherein identifying the candidate lesion region within the acquired ultrasound image based on the GC scores comprises:

removing from the GC score image pixels that have a GC score lower than a first predetermined threshold;

grouping remaining pixels within the GC score image that are connected together into grouped components;

calculating an average GC score for the grouped components; and removing grouped components with averaged GC scores lower than a second predetermined threshold.

10. The method of claim 1, further comprising using the identified candidate lesion region in at least one of a texture-based analysis or a machine learning method to classify the candidate lesion region as a lesion or normal tissue.

11. The method of claim 1, further comprising:

calculating multi-scale topological texture features derived from Minkowski Functional (MF) for the identified candidate lesion region; and classifying the identified candidate lesion region as a lesion or normal tissue.

12. The method of claim 1, wherein generating the FT distribution-based edge feature map comprises applying a Fisher-tippett (FT) distribution-based filter to each of the pixels of the acquired ultrasound image.

13. The method of claim 1, wherein generating the GC scores for the pixels of the acquired ultrasound image comprises generating a GC score for each pixel of the acquired ultrasound image.

14. An ultrasound system, comprising:

an ultrasound transducer for transmitting and receiving ultrasound signals to and from an area of interest;

a receiver for receiving the ultrasound signals;

a processor coupled to the ultrasound probe, the processor programmed to:

acquire an ultrasound image;

generate a Fisher-tippett (FT) distribution-based edge feature map from the acquired ultrasound image;

generate gradient concentration (GC) scores for pixels of the acquired ultrasound image using the FT distribution-based edge feature map; and identify a candidate lesion region within the acquired ultrasound image based on the GC scores; and a display configured to display at least the identified candidate lesion region.

15. The ultrasound system of claim 14, wherein the processor is configured to generate the FT distribution-based edge feature map by applying a distribution-based filter to the pixels of the acquired ultrasound image.

16. The ultrasound system of claim 14, wherein the processor is configured to generate the GC scores using the FT distribution-based edge feature map by a GC filter to the FT distribution-based edge feature map.

17. The ultrasound system of claim 14, wherein the processor is configured to generate the GC scores by assigning a higher weight to relatively high gradient mass boundary pixels than to relatively low gradient noise pixels.

18. The ultrasound system of claim 14, wherein the processor is configured to generate the GC scores using the FT distribution-based edge feature map by assigning a higher GC score to a pixel located within at least one of an ellipsoidal, a hemi-ellipsoidal, or a spherical region of the ultrasound image as compared to a pixel located within a relatively flat region of the ultrasound image.

19. The ultrasound system of claim 14, wherein the processor is configured to generate the GC scores by generating a GC score image, and wherein the processor is configured to identify a candidate lesion region within the acquired ultrasound image based on the GC scores by removing relatively flat tissue from the GC score image.

20. The ultrasound system of claim 14, wherein the processor is configured to generate the GC scores by generating a GC score image, and wherein the processor is configured to identify the candidate lesion region within the acquired ultrasound image based on the GC scores by:

removing from the GC image pixels that have a GC score lower than a first predetermined threshold;

grouping remaining pixels within the GC image that are connected together into grouped components;

calculating an average GC score for the grouped components; and removing grouped components with averaged GC scores lower than a second predetermined threshold.

21. A method for detecting lesions in ultrasound images, said method comprising:

identifying a candidate lesion region within an ultrasound image based on a Fisher-tippett (FT) distribution-based edge feature map;

calculating multi-scale topological texture features for the candidate lesion region from the ultrasound image;

classifying the candidate lesion region as a lesion or normal tissue using a classifier; and displaying at least the classified candidate lesion region.

22. The method of claim 21, wherein calculating multi-scale topological texture features for the candidate lesion region comprises extracting Minkowski Functional (MF)-based texture features for the candidate lesion region.

23. The method of claim 21, wherein calculating multi-scale topological texture features for the candidate lesion region comprises calculating the multi-scale topological texture features on an intensity image.

24. The method of claim 21, wherein calculating multi-scale topological texture features for the candidate lesion region comprises calculating the multi-scale topological texture features on a curvature map.

25. The method of claim 21, wherein classifying the candidate lesion region as a lesion or normal tissue using a classifier comprises classifying the candidate lesion region as a lesion or normal tissue using a Random Forests (RF) classifier.

* * * * *